(12) United States Patent
Kat-Kuoy

(10) Patent No.: US 10,357,264 B2
(45) Date of Patent: Jul. 23, 2019

(54) SHOCK WAVE BALLOON CATHETER WITH INSERTABLE ELECTRODES

(71) Applicant: SHOCKWAVE MEDICAL, INC., Fremont, CA (US)

(72) Inventor: Denny Kat-Kuoy, Santa Rosa, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 233 days.

(21) Appl. No.: 15/370,900

(22) Filed: Dec. 6, 2016

(65) Prior Publication Data

US 2018/0153568 A1    Jun. 7, 2018

(51) Int. Cl.
 A61B 17/22     (2006.01)
 *A61M 25/10*   (2013.01)
 A61M 25/00     (2006.01)

(52) U.S. Cl.
 CPC .. *A61B 17/22022* (2013.01); *A61B 17/22012* (2013.01); *A61M 25/104* (2013.01);
 (Continued)

(58) Field of Classification Search
 CPC ........ A61B 17/22012; A61B 17/22022; A61B 2017/2204; A61B 2017/22025;
 (Continued)

(56) References Cited

U.S. PATENT DOCUMENTS 3,413,976 A    12/1968  Roze
3,785,382 A    1/1974   Schmidt-Kioiber et al.
(Continued)

FOREIGN PATENT DOCUMENTS

AU    2009313507 B2    11/2014
CN       1269708 A      10/2000
(Continued)

OTHER PUBLICATIONS

International Search Report and Written Opinion received for PCT Patent Application No. PCT/US2017/055480, dated Jan. 29, 2018, 14 pages.

(Continued)

*Primary Examiner* — Tuan V Nguyen
(74) *Attorney, Agent, or Firm* — Morrison & Foerster LLP

(57) ABSTRACT

A translatable shock wave treatment apparatus is suitable for use in treating calcified lesions in vascular structures having small diameters. An elongate member carrying a collapsed angioplasty balloon is first inserted into the occluded blood vessel. The angioplasty balloon is inflated with a conducting fluid to pre-dilate the narrow blood vessel prior to introducing electrodes and applying shock wave therapy. After the blood vessel is at least partially opened, a translatable electrode carrier equipped with one or more shock wave emitters is advanced into the angioplasty balloon. Shock waves are then propagated through the fluid to impart energy to calcified plaques along the vessel walls, thereby softening the calcified lesions. Following the shock wave treatment, multiple inflation and deflation cycles of the angioplasty balloon can be administered to gently compress the softened lesion and complete dilation of the blood vessel.

23 Claims, 11 Drawing Sheets

(52) U.S. Cl.
CPC .............. *A61B 2017/22025* (2013.01); *A61B 2017/22051* (2013.01); *A61M 2025/0008* (2013.01)

(58) Field of Classification Search
CPC ...... A61B 2017/22051; A61M 25/104; A61M 2025/0008; A61N 1/38
See application file for complete search history.

(56) References Cited

U.S. PATENT DOCUMENTS

| | | |
|---|---|---|
| 3,902,499 A | 9/1975 | Shene |
| 4,027,674 A | 6/1977 | Tessler et al. |
| 4,030,505 A | 6/1977 | Tessler |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 4,878,495 A | 11/1989 | Grayzel |
| 4,900,303 A | 2/1990 | Lemelson |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,103,804 A | 4/1992 | Abele et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,281,231 A | 1/1994 | Rosen et al. |
| 5,295,958 A | 3/1994 | Shturman |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,505,702 A | 4/1996 | Arney |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | de la Torre et al. |
| 5,846,218 A | 12/1998 | Brisken et al. |
| 5,931,805 A | 8/1999 | Brisken |
| 6,007,530 A | 12/1999 | Dornhofer et al. |
| 6,033,371 A | 3/2000 | Torre et al. |
| 6,080,119 A | 6/2000 | Schwarze et al. |
| 6,083,232 A | 7/2000 | Cox |
| 6,113,560 A | 9/2000 | Simnacher |
| 6,186,963 B1 | 2/2001 | Schwarze et al. |
| 6,210,408 B1 | 4/2001 | Chandrasekaran et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,061 B1 | 8/2002 | Wenner et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,505,812 B1 | 3/2009 | Eggers et al. |
| 7,569,032 B2 | 8/2009 | Naimark et al. |
| 7,618,432 B2 | 11/2009 | Pedersen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,556,813 B2 | 10/2013 | Cioanta et al. |
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,976,371 B2 | 3/2015 | Fukuma |
| 9,005,216 B2 | 4/2015 | Hakala et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,289,224 B2 | 3/2016 | Adams et al. |
| 9,333,000 B2 | 5/2016 | Hakala et al. |
| 2001/0044596 A1 | 11/2001 | Jaafar |
| 2002/0045890 A1 | 4/2002 | Celliers et al. |
| 2002/0177889 A1 | 11/2002 | Brisken et al. |
| 2003/0004434 A1 | 1/2003 | Greco et al. |
| 2003/0163081 A1 | 8/2003 | Constantz et al. |
| 2003/0176873 A1 | 9/2003 | Chernenko et al. |
| 2003/0229370 A1 | 12/2003 | Miller |
| 2004/0044308 A1 | 3/2004 | Naimark et al. |
| 2004/0082859 A1 | 4/2004 | Schaer |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0090846 A1 | 4/2005 | Pedersen et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0077165 A1 | 3/2008 | Murphy |
| 2008/0086073 A1 | 4/2008 | McDaniel |
| 2008/0097251 A1 | 4/2008 | Babaev |
| 2008/0188913 A1 | 8/2008 | Stone et al. |
| 2009/0030503 A1 | 1/2009 | Ho |
| 2009/0041833 A1 | 2/2009 | Bettinger et al. |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |

(56) References Cited

U.S. PATENT DOCUMENTS

| | | | |
|---|---|---|---|
| 2010/0204712 A1* | 8/2010 | Mallaby | A61B 17/22 606/128 |
| 2010/0305565 A1 | 12/2010 | Truckai et al. | |
| 2010/0324554 A1 | 12/2010 | Gifford et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0208185 A1 | 8/2011 | Diamant et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0116289 A1 | 5/2012 | Hawkins et al. | |
| 2012/0143177 A1 | 6/2012 | Avitall | |
| 2012/0203255 A1 | 8/2012 | Hawkins et al. | |
| 2012/0221013 A1 | 8/2012 | Hawkins et al. | |
| 2012/0253358 A1 | 10/2012 | Golan | |
| 2013/0030431 A1 | 1/2013 | Adams | |
| 2013/0030447 A1 | 1/2013 | Adams | |
| 2013/0116714 A1 | 5/2013 | Adams et al. | |
| 2014/0005576 A1 | 1/2014 | Adams et al. | |
| 2014/0039513 A1 | 2/2014 | Hakala et al. | |
| 2014/0039514 A1 | 2/2014 | Adams et al. | |
| 2014/0046229 A1* | 2/2014 | Hawkins | A61H 23/008 601/46 |
| 2014/0046353 A1 | 2/2014 | Adams | |
| 2014/0052145 A1 | 2/2014 | Adams et al. | |
| 2014/0052147 A1 | 2/2014 | Hakala et al. | |
| 2014/0074111 A1 | 3/2014 | Hakala et al. | |
| 2014/0074113 A1 | 3/2014 | Hakala et al. | |
| 2014/0163592 A1 | 6/2014 | Hawkins et al. | |
| 2014/0214061 A1 | 7/2014 | Adams et al. | |
| 2014/0243820 A1 | 8/2014 | Adams et al. | |
| 2014/0243847 A1 | 8/2014 | Hakala et al. | |
| 2014/0288570 A1 | 9/2014 | Adams | |
| 2015/0073430 A1 | 3/2015 | Hakala et al. | |
| 2015/0238208 A1 | 8/2015 | Adams et al. | |
| 2015/0238209 A1 | 8/2015 | Hawkins et al. | |
| 2015/0320432 A1 | 11/2015 | Adams | |
| 2016/0135828 A1 | 5/2016 | Hawkins et al. | |
| 2016/0151081 A1 | 6/2016 | Adams et al. | |
| 2016/0183957 A1 | 6/2016 | Hakala et al. | |
| 2016/0324534 A1 | 11/2016 | Hawkins et al. | |
| 2018/0028208 A1 | 2/2018 | Adams et al. | |

FOREIGN PATENT DOCUMENTS

| | | |
|---|---|---|
| CN | 101043914 A | 9/2007 |
| CN | 102057422 A | 5/2011 |
| CN | 102271748 A | 12/2011 |
| CN | 102765785 A | 11/2012 |
| DE | 3038445 A1 | 5/1982 |
| EP | 0442199 A2 | 8/1991 |
| EP | 0571306 A1 | 11/1993 |
| EP | 2362798 B1 | 4/2014 |
| JP | 60-191353 U | 12/1985 |
| JP | 62-99210 U | 6/1987 |
| JP | 62-275446 A | 11/1987 |
| JP | 3-63059 A | 3/1991 |
| JP | 6-125915 A | 5/1994 |
| JP | 7-47135 A | 2/1995 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004-81374 A | 3/2004 |
| JP | 2004-357792 A | 12/2004 |
| JP | 2005-95410 A | 4/2005 |
| JP | 2005-515825 A | 6/2005 |
| JP | 2006-516465 A | 7/2006 |
| JP | 2007-532182 A | 11/2007 |
| JP | 2008-506447 A | 3/2008 |
| JP | 2011-520248 A | 7/2011 |
| JP | 2011-524203 A | 9/2011 |
| JP | 2011-528963 A | 12/2011 |
| JP | 2012-508042 A | 4/2012 |
| WO | 1989/011307 A1 | 11/1989 |
| WO | 1996/24297 A1 | 8/1996 |
| WO | 1999/02096 A1 | 1/1999 |
| WO | 2004/069072 A2 | 8/2004 |
| WO | 2005/099594 A1 | 10/2005 |
| WO | 2006/006169 A2 | 1/2006 |
| WO | 2006/127158 A2 | 11/2006 |
| WO | 2007/088546 A2 | 8/2007 |
| WO | 2007/149905 A2 | 12/2007 |
| WO | 2009/121017 A1 | 10/2009 |
| WO | 2009/126544 A1 | 10/2009 |
| WO | 2009/152352 A2 | 12/2009 |
| WO | 2010/014515 A2 | 2/2010 |
| WO | 2010/014515 A3 | 8/2010 |
| WO | 2010/054048 A3 | 9/2010 |
| WO | 2011/069025 A1 | 6/2011 |
| WO | 2011/143468 A2 | 11/2011 |
| WO | 2012/025833 A2 | 3/2012 |
| WO | 2013/070750 A1 | 5/2013 |
| WO | 2014/025620 A1 | 2/2014 |
| WO | 2016/077627 A1 | 5/2016 |

OTHER PUBLICATIONS

Non-Final Office Action received for U.S. Appl. No. 15/018,160, dated Apr. 7, 2017, 10 pages.
Notice of Allowance received for U.S. Appl. No. 15/018,160, dated Jul. 14, 2017, 7 pages.
Advisory Action received for U.S. Appl. No. 13/615,107, dated Nov. 6, 2015, 3 pages.
Advisory Action received for U.S. Appl. No. 14/229,735, dated Nov. 3, 2015, 3 pages.
Advisory Action Received for U.S. Appl. No. 12/482,995, dated Jun. 2, 2014, 3 pages.
Advisory Action Received for U.S. Appl. No. 12/482,995, dated Sep. 29, 2011, 2 pages.
Advisory Action Received for U.S. Appl. No. 12/581,295, dated Jul. 3, 2014, 3 pages.
Advisory Action Received for U.S. Appl. No. 13/049,199, dated Jun. 7, 2012, 3 pages.
Advisory Action received for U.S. Appl. No. 13/267,383, dated Jan. 6, 2014, 4 pages.
Decision of Appeals Notice received for Japanese Patent Application No. 2011534914, dated Oct. 17, 2016, 2 pages (Official Copy Only) (See Communication under 37 CFR § 1.98(a) (3)).
Decision to Grant received for European Patent Application No. 13756766.5, dated May 27, 2016, 2 pages.
Decision to Grant received for European Patent Application No. 09825393.3, dated Mar. 13, 2014, 2 pages.
Decision to Grant received for European Patent Application No. 13748228.7, dated Aug. 25, 2016, 2 pages.
Decision to Grant received for Japanese Patent Application No. 2011-513694, dated Oct. 7, 2014, 3 pages (Official Copy Only) (See Communication under 37 CFR § 1.98(a) (3)).
Extended European Search Report (includes Supplementary European Search Report and Search Opinion) received for European Patent Application No. 09763640.1, dated Oct. 10, 2013, 5 pages.
Extended Eumpeen Search Report and Search Opinion received for EP Patent Appiieaiion No. 098253933, dated Feb. 28, 2013, 6 pages.
Extended European Search Report received for European Patent Application No. 13827971.6, dated Apr. 12, 2016, 8 pages.
Final Office Action received for U.S. Appl. No. 12/482,995, dated Jul. 22, 2011, 14 pages.
Final Office Action received for U.S. Appl. No. 12/601,619, dated Feb. 21, 2012, 12 pages.
Final Office Action received for U.S. Appl. No. 12/611,997, dated Dec. 11, 2012, 9 pages.
Final Office Action received for U.S. Appl. No. 12/611,997, dated Nov. 10, 2011, 15 pages.
Final Office Action received for U.S. Appl. No. 13/049,199, dated Apr. 4, 2012, 10 pages.
Final Office Action received for U.S. Appl. No. 13/207,381, dated Nov. 2, 2012, 7 pages.

(56) References Cited

OTHER PUBLICATIONS

Final Office Action received for U.S. Appl. No. 14/271,342, dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 12/611,997, dated Oct. 24, 2013, 10 pages.
Final Office Action received for U.S. Appl. No. 13/049,199, dated Aug. 11, 2014, 8 pages.
Final Office Action received for U.S. Appl. No. 13/207,381, dated Nov. 7, 2013, 7 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107, dated Sep. 1, 2015, 9 pages.
Final Office Action received for U.S. Appl. No. 13/646,570, dated Dec. 23, 2014, 10 pages.
Final Office Action received for U.S. Appl. No. 14/229,735, dated Aug. 27, 2015, 7 pages.
Intention to Grant received for European Patent Application No. 13748228.7, dated Mar. 23, 2016, 5 pages.
Intention to Grant received for European Patent Application No. 13756766.5, dated Jan. 8, 2016, 5 pages.
International Preliminary Report on Patentability received for PCT Patent Application No. PCT/US2011/051606, dated May 14, 2013, 6 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2009/063354, dated May 19, 2011, 6 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2012/063925, dated May 22, 2014, 12 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987, dated Nov. 20, 2014, 11 pages.
International Preliminary Report on Patentability received for PCT Patent Application No. PCT/US2013/048277, dated Jan. 8, 2015, 9 pages.
International Preliminary Report on Patentability received for PCT Patent Application No. PCT/US2013/053292, dated Feb. 19, 2015, 9 pages.
International Preliminary Report on Patentability received for PCT Patent Application No. PCT/US2013/054104, dated Feb. 19, 2015, 8 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533, dated Mar. 26, 2015, 10 pages.
International Search Report and Written Opinion received for PCT Patent Application No. PCT/US2011/051606, dated Apr. 24, 2012, 9 pages.
International Search Report and Written Opinion received for PCT Patent Application No. PCT/US2013/031805, dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/053292, dated Nov. 4, 2013, 14 pages.
International Search Report and Written Opinion received for PCT Patent Application No. PCT/US2013/054104, dated Oct. 22, 2013, 12 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088, dated Jul. 16, 2015, 13 pages.
International Search Report and Written Opinion received for PCT Patent Application No. PCT/US2015/060453, dated Jan. 21, 2016, 15 pages.
International Search Report received for PCT Patent Application No. PCT/US2009/047070, dated Jan. 19, 2010, 4 pages.
International Search Report received for PCT Patent Application No. PCT/US2009/063354, dated Jun. 11, 2010, 3 pages.
International Search Report received for PCT Patent Application No. PCT/US2012/023172, dated Sep. 28, 2012, 3 pages.
International Search Report received for PCT Patent Application No. PCT/US2012/063925, dated Mar. 25, 2013, 3 pages.
International Written Opinion received for PCT Patent Application No. PCT/US2009/063354, dated Jun. 11, 2010, 4 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
International Written Opinion received for PCT Patent Application No. PCT/US2012/063925, dated Mar. 25, 2013, 9 pages.
International Written Opinion received for PCT Patent Application No. PCT/US2009/047070, dated Jan. 19, 2010, 5 pages.
Non Final Office Action received for U.S. Appl. No. 12/482,995, dated Aug. 13, 2014, 10 pages.
Non Final Office Action received for U.S. Appl. No. 12/482,995, dated Jul. 12, 2013, 11 pages.
Non Final Office Action received for U.S. Appl. No. 12/611,997, dated Nov. 26, 2014, 8 pages.
Non Final Office Action received for U.S. Appl. No. 13/207,381, dated Nov. 25, 2014, 5 pages.
Non Final Office Action received for U.S. Appl. No. 13/465,264, dated Oct. 29, 2014, 13 pages.
Non Final Office Action received for U.S. Appl. No. 13/646,570, dated Oct. 29, 2014, 10 pages.
Non Final Office Action received for U.S. Appl. No. 14/079,463, dated Mar. 4, 2014, 9 pages.
Non Final Office Action received for U.S. Appl. No. 14/229,735, dated May 7, 2015, 8 pages.
Non Final Office Action received for U.S. Appl. No. 12/482,995, dated Feb. 11, 2011, 27 pages.
Non Final Office Action received for U.S. Appl. No. 12/501,619, dated Nov. 3, 2011, 10 pages.
Non Final Office Action received for U.S. Appl. No. 12/611,997, dated Apr. 8, 2013, 9 pages.
Non Final Office Action received for U.S. Appl. No. 12/611,997, dated Aug. 24, 2012, 11 pages.

(56) References Cited

OTHER PUBLICATIONS

Non Final Office Action received for U.S. Appl. No. 12/611,997, dated Jun. 21, 2011, 13 pages.
Non Final Office Action received for U.S. Appl. No. 13/049,199, dated Dec. 12, 2011, 10 pages.
Non Final Office Action received for U.S. Appl. No. 13/207,381, dated Feb. 22, 2013, 7 pages.
Non Final Office Action received for U.S. Appl. No. 13/207,381, dated Jun. 12, 2012, 6 pages.
Non Final Office Action received for U.S. Appl. No. 13/232,730, dated Apr. 23, 2013, 10 pages.
Non Final Office Action received for U.S. Appl. No. 13/291,875, dated Feb. 28, 2013, 8 pages.
Non Final Office Action received for U.S. Appl. No. 13/534,658, dated Mar. 11, 2016, 12 pages.
Non Final Office Action received for U.S. Appl. No. 14/218,858, dated Mar. 30, 2016, 13 pages.
Non Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 12/611,997, dated Feb. 13, 2014, 9 pages.
Non-Final Office Action received for U.S. Appl. No. 13/049,199, dated Feb. 4, 2014, 8 pages.
Non-Final Office Action received for U.S. Appl. No. 13/207,381, dated Feb. 25, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 13/962,315, dated Aug. 26, 2015, 20 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 14/273,063, dated Jun. 3, 2016, 9 pages.
Non-Final Office Action received for U.S. Appl. No. 14/693,155, dated Jan. 15, 2016, 6 pages.
Notice of Acceptance Received for Australian Patent Application No. 2009257368, dated Aug. 28, 2014, 2 pages.
Notice of Acceptance Received for Australian Patent Application No. 2009313507, dated Nov. 17, 2014, 2 pages.
Notice of Allowance received for Canadian Patent Application No. 2,727,429, dated May 26, 2015, 1 page.
Notice of Allowance received for U.S. Appl. No. 14/229,735, dated Nov. 17, 2015, 5 pages.
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 12/611,997, dated Apr. 15, 2015, 7 pages.
Notice of Allowance received for U.S. Appl. No. 13/207,381, dated Apr. 14, 2015, 7 pages.
Notice of Allowance received for U.S. Appl. No. 13/465,264, dated May 8, 2015, 7 pages.
Notice of Allowance received for U.S. Appl. No. 13/957,276, dated Aug. 28, 2015, 9 pages.
Notice of Allowance received for U.S. Appl. No. 14/046,635, dated Dec. 17, 2013, 7 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/291,875, dated Sep. 17, 2013, 11 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 14/693,155, dated Apr. 26, 2016, 9 pages.
Notice of Allowance received for U.S. Appl. No. 13/615,107, dated Dec. 31, 2015, 10 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Australian Patent Application No. 2009313507, dated Nov. 13, 2013, 3 pages.
Office Action received for Canadian Patent Application No. 2,727,429, dated Apr. 14, 2015, 4 pages.
Office Action received for Canadian Patent Application No. 2,779,600, dated Jan. 4, 2016, 6 pages.
Office Action received for Chinese Patent Application No. 200980153687.X, dated Dec. 26, 2012, 11 pages (Official Copy Only) (See Communication under 37 CFR § 1.98(a) (3)).
Office Action received for Chinese Patent Application No. 200980153687.X, dated Jul. 11, 2013, 11 pages (Official Copy Only) (See Communication under 37 CFR § 1.98(a) (3)).
Office Action received for Chinese Patent Application No. 201380033808.3, dated Jul. 5, 2016, 9 pages (3 pages of English translation and 6 pages of Official Copy).
Office Action received for Chinese Patent Application No. 201380041288.0, dated Jun. 20, 2016, 7 pages (4 pages of English Translation and 3 pages of Official Copy).
Office Action received for Chinese Patent Application No. 201380041656.1, dated Jul. 5, 2016, 9 pages (4 pages of English Translation and 5 pages of Official Copy).
Office Action received for Japanese Patent Application No. 2011-513694, dated Aug. 27, 2013, 6 pages (3 pages of English Translation and 3 pages of Official Copy).
Office Action Received for Japanese Patent Application No. 2011-534914, dated Jan. 13, 2015, 9 pages (7 pages of English Translation and 2 pages of Official Copy).
Office Action Received for Japanese Patent Application No. 2011-534914, dated Jul. 15, 2014, 3 pages (1 page of English Translation and 2 pages of Official Copy).
Office Action received for Japanese Patent Application No. 2011-534914, dated May 10, 2016, 10 pages (6 pages of English Translation and 4 pages of Official Copy).

(56) References Cited

OTHER PUBLICATIONS

Office Action received for Japanese Patent Application No. 2011-534914, dated Oct. 1, 2013, 5 pages (2 pages of English Translation and 3 pages of Official Copy).
Office Action Received for Japanese Patent Application No. 2014-158517, dated May 19, 2015, 5 pages (2 pages of English Translation and 3 pages of Official Copy).
Office Action received for Japanese Patent Application No. 2015-036444, dated Feb. 23, 2016, 3 pages (English Translation Only).
Office Action received for Japanese Patent Application No. 2015-036444, dated Sep. 14, 2016, 5 pages (3 Pages of English Translation and 2 Pages of Official Copy).
Rosenschein et al., "Shock-Wave Thrombus Ablation, a New Method for Noninvasive Mechanical Thrombolysis", The American Journal of Cardiology, vol. 70, No. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.

* cited by examiner

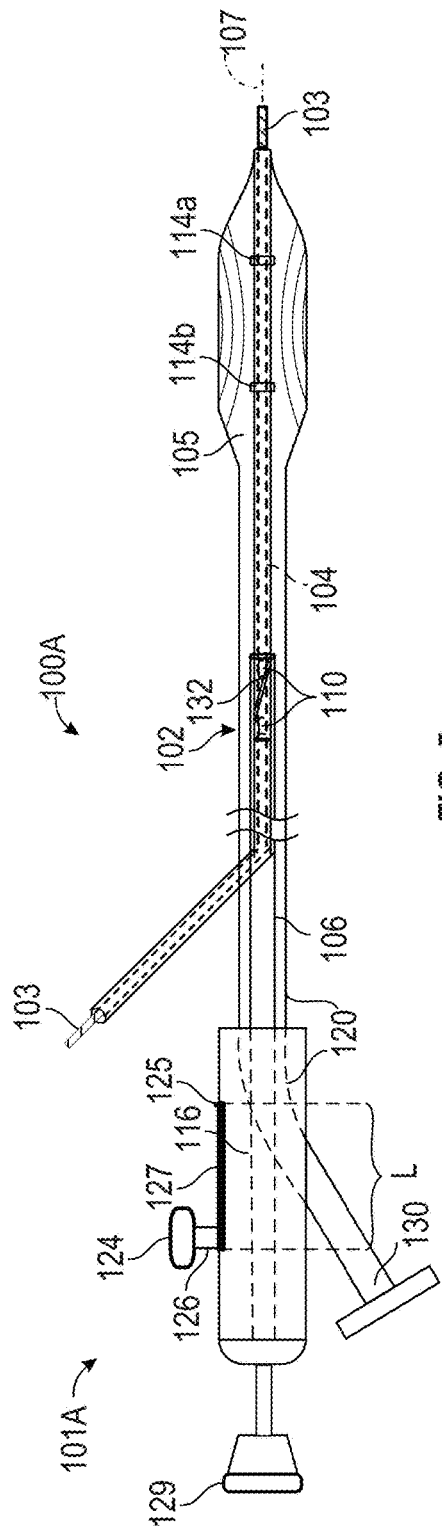
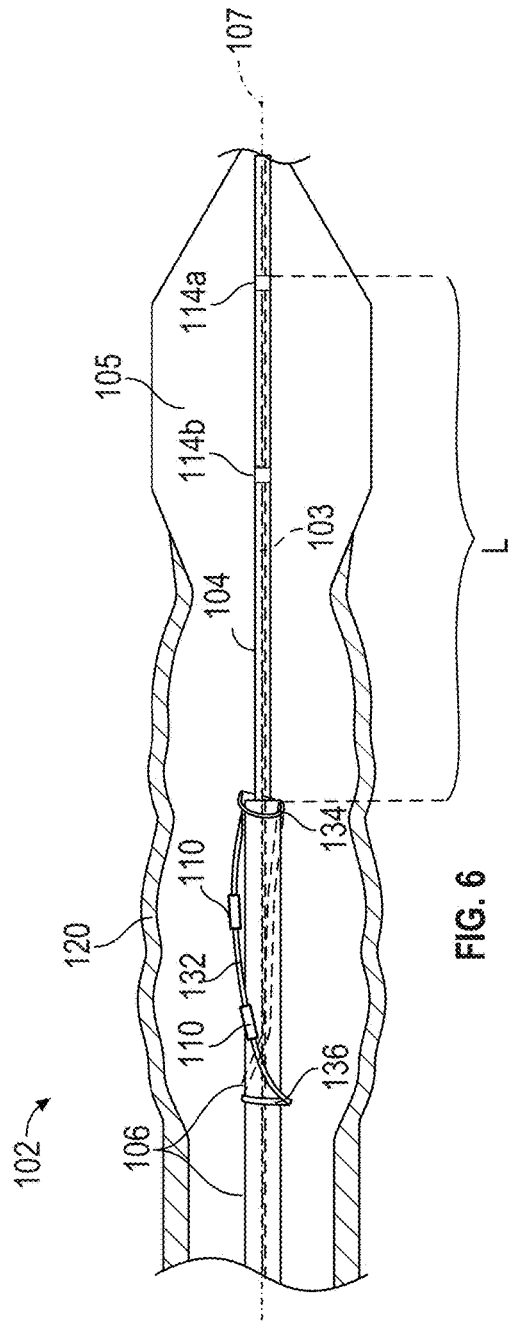
FIG. 5
FIG. 6

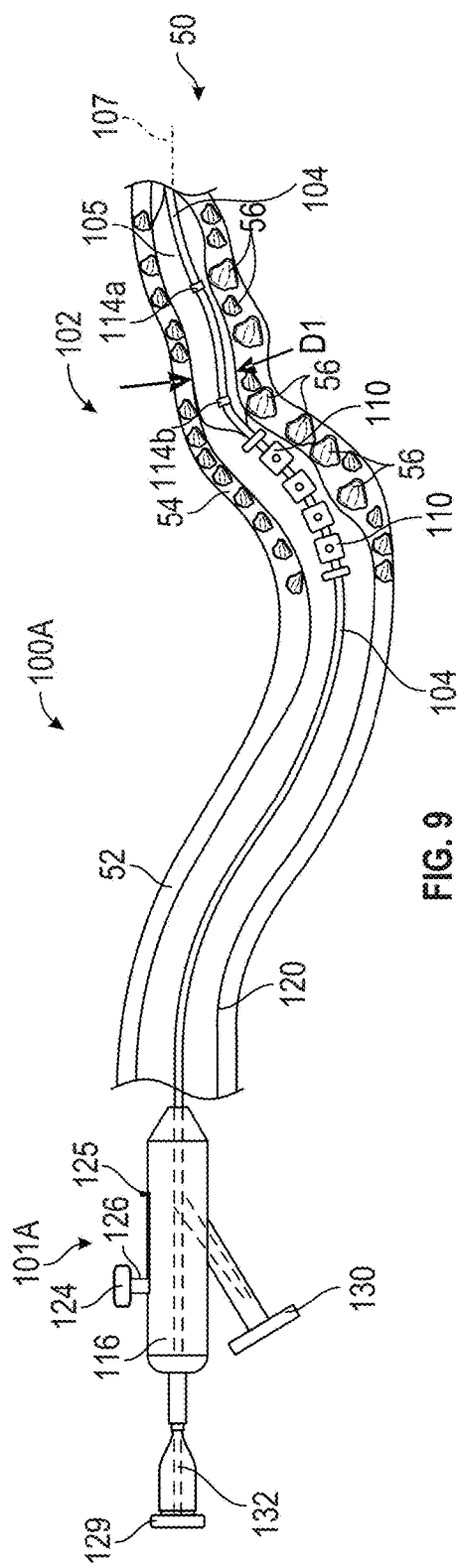
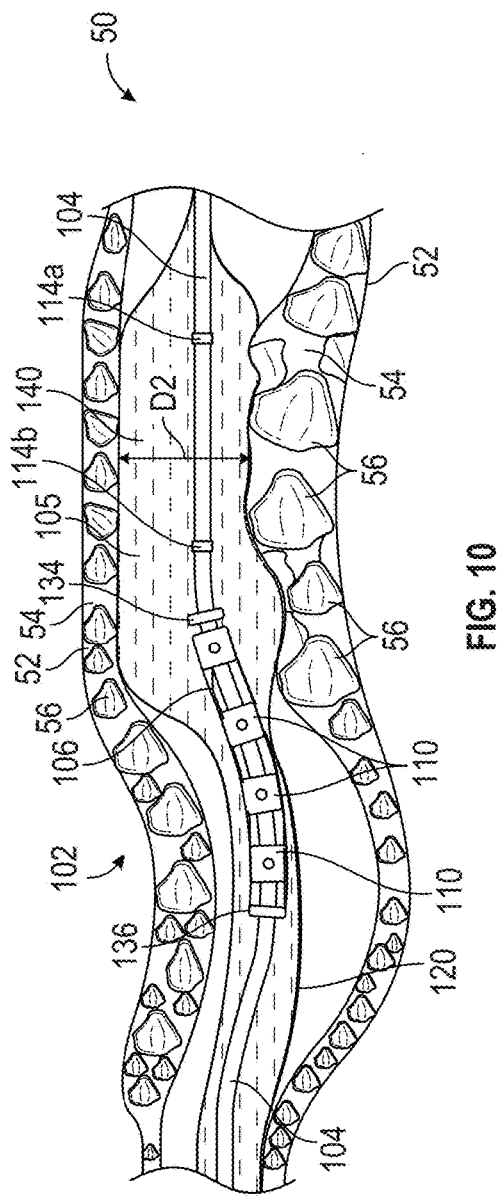

SHOCK WAVE BALLOON CATHETER WITH INSERTABLE ELECTRODES

FIELD

The present disclosure relates generally to occlusions in human vascular structures and, in particular, to the use of shock wave therapy in the treatment of calcified lesions.

BACKGROUND

Balloon angioplasty is a well-known, standard treatment that restores blood flow in blocked arteries. Blockages occur when plaque accumulates in the walls of the blood vessels, forming lesions. In a conventional balloon angioplasty procedure, a catheter carrying an angioplasty balloon is inserted into the blood vessel along a guide wire to position the angioplasty balloon adjacent to a lesion. Progress of the guide wire may be tracked using fluoroscopy or x-rays. Inflating the angioplasty balloon compresses soft lesions on the wall of the vessel, thereby dilating the blood vessel and allowing blood to flow through a larger portion thereof. However, when plaque is hardened, or calcified, gentle compression may not be effective. In such cases, rapid expansion of the angioplasty balloon may occur when the calcified lesions break, so as to permit increasing the inner diameter of the blood vessel. Conventional balloon angioplasty techniques used to treat such calcified lesions may impart high stress that can damage vessel walls. Soft tissue damage often includes dissections or perforations that require placement of a stent to restore structural integrity to the blood vessel wall.

An improved electrohydraulic dilation technique has been used to treat calcified plaques using shock waves. Lithoplasty® technology is described in U.S. Pat. Nos. 8,956,371 and 8,888,788, assigned to Shockwave, Inc., of Fremont, Calif., both of which are incorporated by reference herein in their entireties. In this technique, electrodes are disposed inside the angioplasty balloon. The angioplasty balloon is inflated with a conductive fluid, for example, a saline solution, which will propagate shock waves, i.e., high energy pressure waves. When high voltage pulsed signals are applied to a bipolar emitter, i.e., a pair of emitter electrodes, a resulting plasma arc creates a rapidly expanding and collapsing gas bubble that emits a shock wave through the fluid. When a unipolar emitter is used, the high voltage signal arcs between a single emitter electrode and the fluid itself. Such shock waves have been shown to effectively break up, dislodge, or pulverize hardened plaques, thereby softening the lesion while preserving the integrity of the vessel walls. Following shock wave treatment, a conventional low-pressure angioplasty procedure can be used effectively to gently compress the softened lesions and dilate the blood vessel.

BRIEF SUMMARY

While existing cardiovascular intervention therapies are appropriate for treating calcified lesions in larger blood vessels, e.g., leg arteries having diameters of about 5.0-10.0 mm, smaller vascular structures, or those that are severely blocked may not have a sufficient diameter to accommodate a Lithoplasty® apparatus. Such smaller vascular structures include, for example, cerebral and coronary arteries having diameters less than about 3.0 mm.

A translatable shock wave treatment apparatus is suitable for use in treating small diameter blood vessels that contain calcified lesions. According to a new procedure, an elongate member, or catheter, carrying a folded or collapsed angioplasty balloon is first inserted into the narrow blood vessel. The collapsed angioplasty balloon has a small diameter that will fit into the narrow blood vessel. The angioplasty balloon is then inflated with a conducting fluid to pre-dilate the narrow blood vessel prior to introducing electrodes and applying shock wave therapy. After the blood vessel is at least partially opened, a translatable electrode carrier equipped with one or more shock wave emitters is advanced along the catheter from an initial position outside the balloon to a destination position inside the balloon. Shock waves are then propagated through the fluid to impart energy to calcified plaques along the vessel walls, thereby softening the calcified lesions. Following the shock wave treatment, the angioplasty balloon can be further inflated to gently compress the softened lesion and complete dilation of the blood vessel. In heavily occluded blood vessels, shock wave therapy can be used multiple times—first, to pre-dilate the blood vessel, and then, alternating with inflation of the angioplasty balloon, to open the blood vessel.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 5 is a side elevation view of the translatable shock wave treatment apparatus of FIGS. 3A-3D in an initial position.

FIG. 6 is a cross-sectional view of a distal end of the translatable shock wave treatment apparatus of FIGS. 3A-3D.

FIGS. 9-13 are side elevation views of the translatable shock wave treatment apparatus in use at various steps of the method shown in FIG. 8.

FIG. 9 is a side elevation view of the translatable shock wave treatment apparatus in use, prior to inflating the angioplasty balloon.

FIG. 10 is a side elevation view of the translatable shock wave treatment apparatus in use, after partially inflating the angioplasty balloon with a fluid.

FIG. 11 is a side elevation view of the translatable shock wave treatment apparatus in use, during shock wave emission.

FIG. 12 is a magnified side elevation view of the translatable shock wave treatment apparatus in use, during shock wave emission.

FIG. 13 is a side elevation view of the translatable shock wave treatment apparatus in use, following treatment of calcified lesions.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another, not to imply a priority of one element over the other. For example, a first marker could be termed a second marker, and, similarly, a second marker could be termed a first marker, without departing from the scope of the various described embodiments. The first marker and the second marker are both markers, but they are not the same marker.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. The term "and/or" as used herein refers to and encompasses any and all possible combinations of one or more of the associated listed items. The terms "includes," "including," "comprises," and/or "comprising," when used in this specification, specify the presence of stated features, steps, operations, elements, and/or components, but do not preclude the presence or addition of one or more other features, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 1:
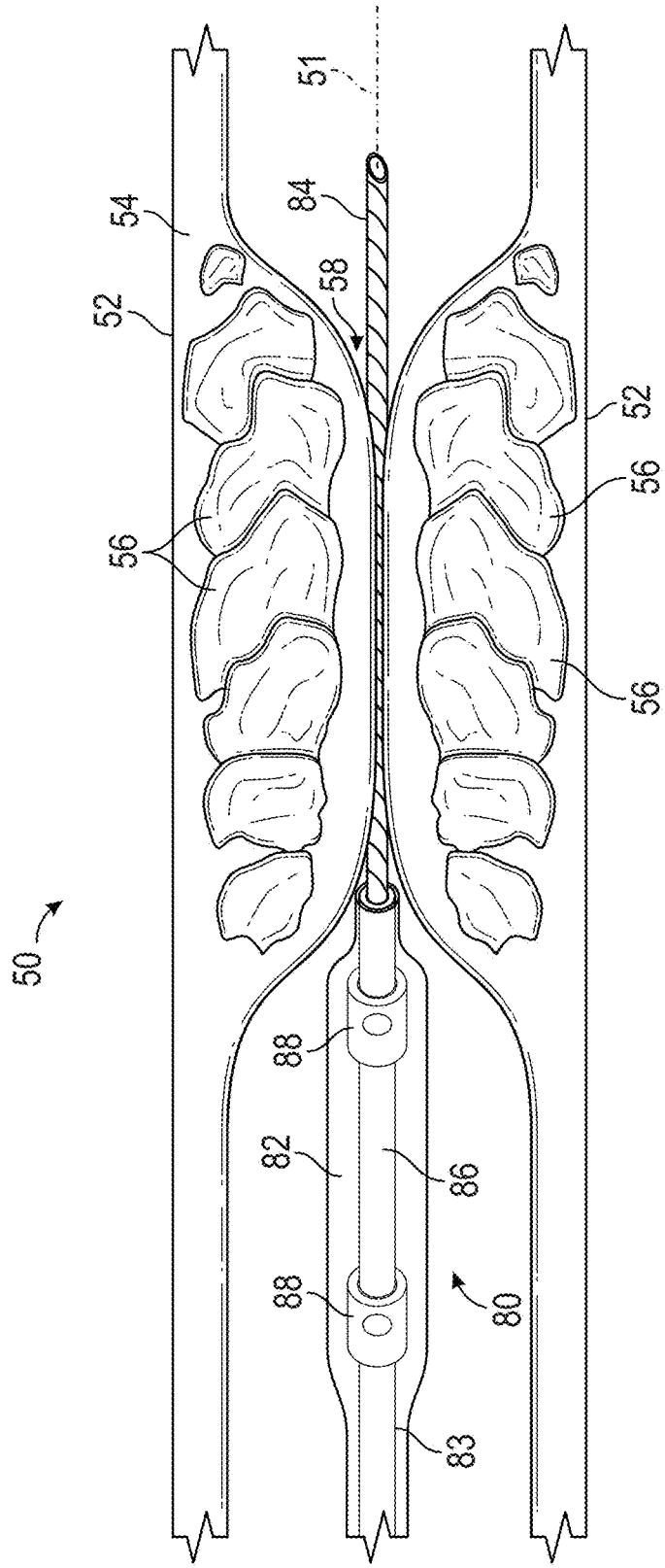
FIG. 1 is a cross-sectional view of an existing shock wave balloon catheter apparatus, according to the prior art.

Turning now to the drawings, FIG. 1 illustrates an exemplary vascular structure, e.g., a blood vessel 50 representing an artery, having a central axis 51 and a vessel wall 52. The representative blood vessel 50 is occluded by a region of plaque, or lesion 54 that has formed in the vessel wall 52. The lesion 54 may include hardened plaque deposits e.g., calcifications 56. Such lesions 54 may be located in other types of vascular structures such as, for example, a valve in a blood vessel, or a heart valve. In the example shown in FIG. 1, lesions 54 extend from opposite vessel walls 52 far enough into the center of the blood vessel 50 that blood flow is almost fully obstructed. Only a narrow opening 58 remains along the central axis 51.

FIG. 1 further illustrates an attempt to insert an existing shock wave treatment apparatus 80 into the occluded blood vessel 50, according to an existing method of treatment. The existing shock wave treatment apparatus 80 having an angioplasty balloon 82, a shock wave guide wire lumen 83, a guide wire 84, an electrode carrier 86, and electrodes 88. The angioplasty balloon 82 and the electrode carrier 86 are coaxial with the guide wire lumen 83 and the guide wire 84. The angioplasty balloon 82 is initially folded over the guide wire lumen 83. In the example shown, the electrodes 88 are shown as cylinders, co-axial with the electrode carrier 86. Each electrode 88 may represent a uni-polar electrode or a pair of bi-polar electrodes, both of which are known in the art.

According to an existing method of treatment, a leading end of the guide wire 84 is inserted through the narrow opening 58, followed by the shock wave treatment apparatus 80 bearing the folded angioplasty balloon 82. Once the shock wave treatment apparatus 80 is positioned adjacent to the calcifications 56 to be treated, treatment can be initiated. However, in the situation shown in FIG. 1, the opening 58 is very narrow. Consequently, the shock wave treatment apparatus 80 is too large, relative to the opening 58, to be safely advanced into the occluded region, even when the balloon is deflated. For example, the shock wave treatment apparatus 80 may have a diameter of about 0.044 inches, or approximately 1.0 mm. This problem arises, for example, when the blood vessel 50 has a narrow diameter, e.g., a few millimeters, or whenever the lesions 54 are localized so that the diameter of the blood vessel opening 58 is abruptly reduced to about 1.0 mm or less.

FIGS. 2-7 illustrate a translatable shock wave treatment apparatus 90, according to some embodiments of the present disclosure. Two exemplary embodiments of the translatable shock wave treatment apparatus 90 are shown in FIGS. 2A, 2B, having respective catheter systems 100A,B respective handle assemblies 101A,B, an emitter assembly 102, a guide wire 103, a guide wire lumen 104, an angioplasty balloon 105, and an electrode carrier 106. The handle assembly 101A/B defines a proximal end of the translatable shock wave treatment apparatus 90. The angioplasty balloon 105 is attached to a distal end of the translatable shock wave treatment apparatus 90, opposite the handle assembly 101A/B at the proximal end. The guide wire lumen 104 is a hollow tube containing the guide wire 103. The guide wire lumen 104, or elongate member of the translatable shock wave treatment apparatus 90, extends between the distal end and the handle assembly along a central axis 107. The emitter assembly 102 is mounted to a distal end of the electrode carrier 106 for translation along the elongate member, relative to the angioplasty balloon 105. The elongate member is semi-rigid but also flexible, permitting insertion into a blood vessel. The angioplasty balloon 105 has a known structure and is made of a known material, e.g., a bio-compatible flexible material that is used in conventional angioplasty procedures. The guide wire lumen 104 and the guide wire 103 also have conventional structures and are made of biocompatible materials that may safely be introduced into a human bloodstream.

Figure 2A:
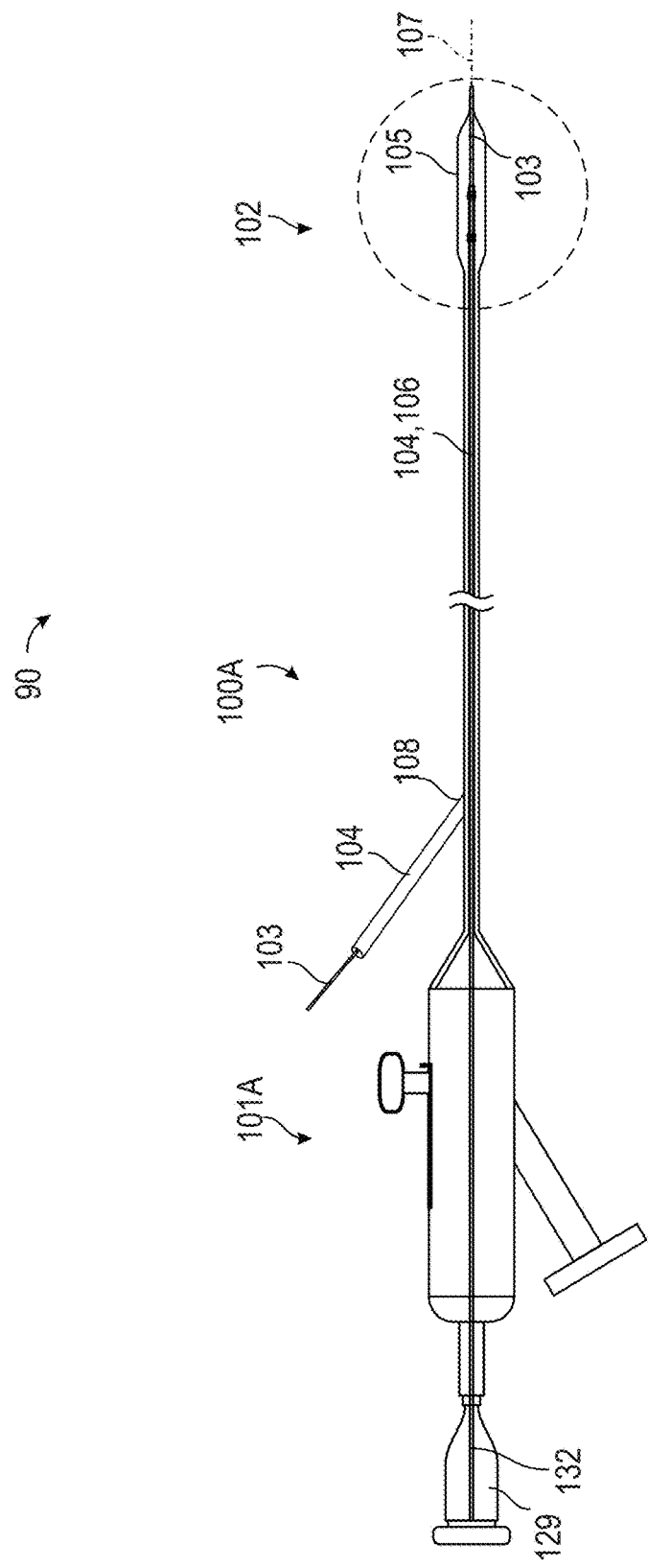
FIG. 2A is a side view of a translatable shock wave treatment apparatus according to some embodiments of the present disclosure, as described herein.

FIG. 2A illustrates a first embodiment of the translatable shock wave treatment apparatus 90, in which the guide wire 103 joins the catheter system 100A at a sealed entry port 108. The catheter system 100A is known in the art as a rapid exchange (Rx) system. The handle assembly 101A includes an electrical connector 129 that transmits electrical power to the emitter assembly 102 via wires 132. The handle assembly 101A is configured to translate the emitter assembly 102 with respect to the angioplasty balloon 105.

Figure 2B:
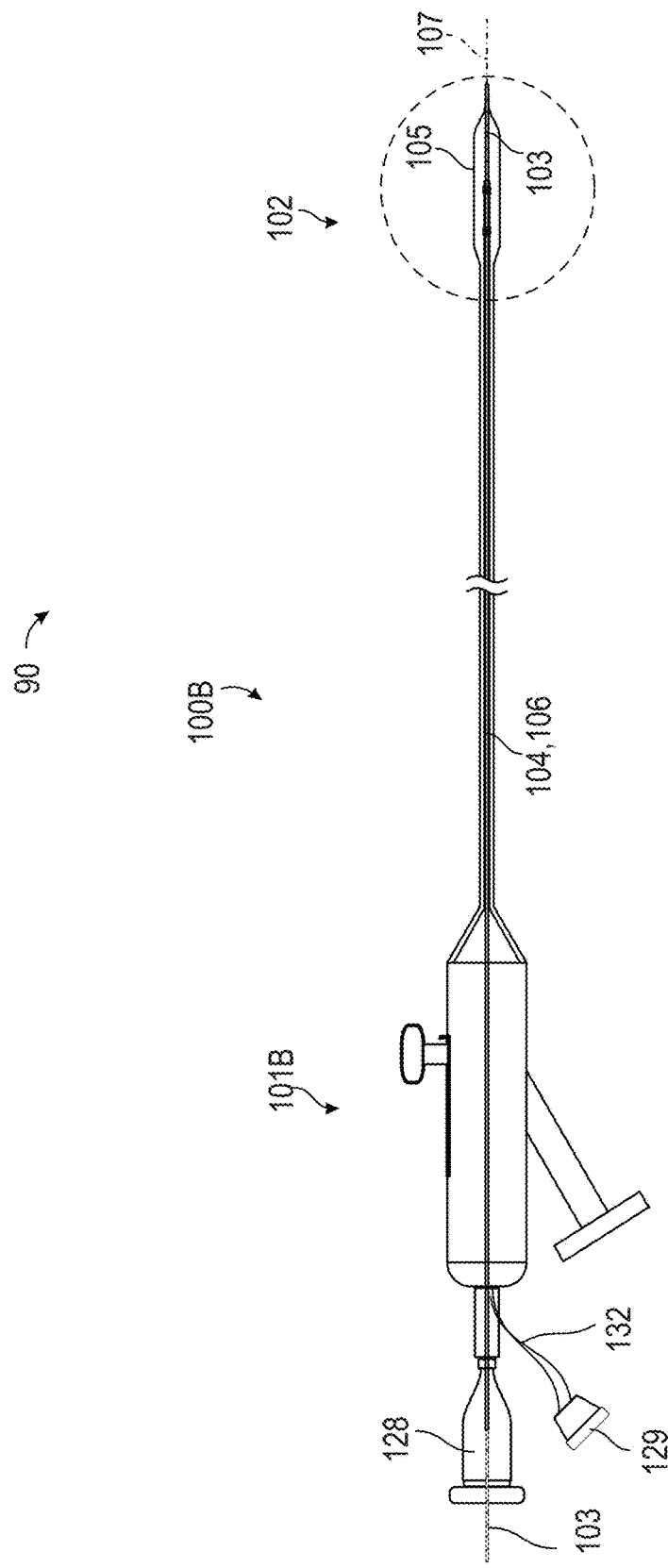
FIG. 2B is a side view of a translatable shock wave treatment apparatus according to some embodiments of the present disclosure, as described herein.

FIG. 2B illustrates a second embodiment of the translatable shock wave treatment apparatus 90, in which the guide wire 103 extends all the way through the catheter system 100B, including the handle assembly 101B. The catheter system 100B is known in the art as an over-the-wire system. The handle assembly 101B includes a guide wire handle 128 that can be used to extend and retract the guide wire 103. The handle assembly 101B also includes an electrical connector 129 that transmits electrical power to the emitter assembly 102 via the wires 132. Either one of the rapid exchange system 100A or the over-the-wire system 100B can be equipped with the emitter assembly 102, the electrode carrier 106, and either handle assembly 101A, or 101B to permit translation of the emitter assembly 102 into and out of the angioplasty balloon 105.

Figure 3A:
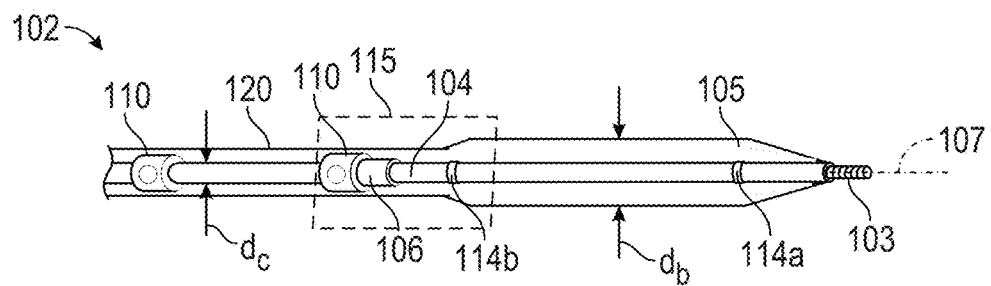
FIGS. 3A, 3B, 3C, and 3D show side views, magnified views, and an end view, respectively, of a translatable shock wave treatment apparatus according to some embodiments of the present disclosure, as described herein.
Figure 3B:
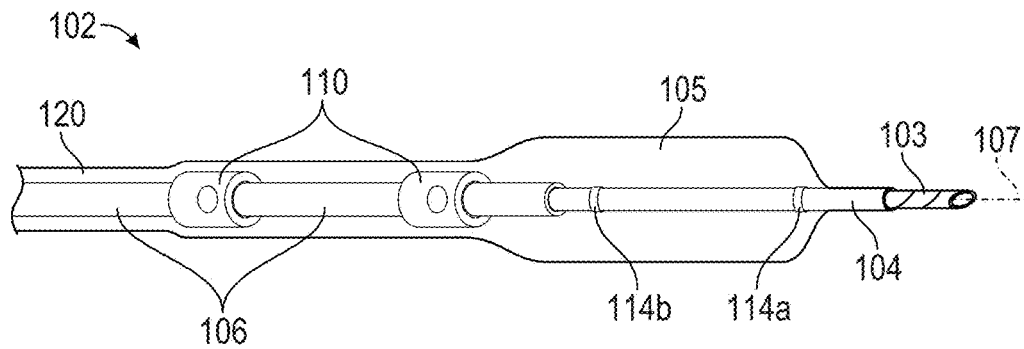

FIGS. 3A and 3B show magnified views of the distal end of the translatable shock wave treatment apparatus 90, in which the guide wire lumen 104 supports the emitter assembly 102 and the angioplasty balloon 105, according to some embodiments of the present disclosure. In FIG. 3A, the electrode carrier 106 is outside the angioplasty balloon 105. The angioplasty balloon 105 is folded over the guide wire lumen 104 so that the guide wire lumen 104 bearing the collapsed balloon has a narrow profile and a diameter $d_b$. The diameter $d_b$ may be compressible. In FIG. 3B, the electrode carrier 106 is outside the angioplasty balloon 105 and the angioplasty balloon 105 is inflated.

Figure 3C:
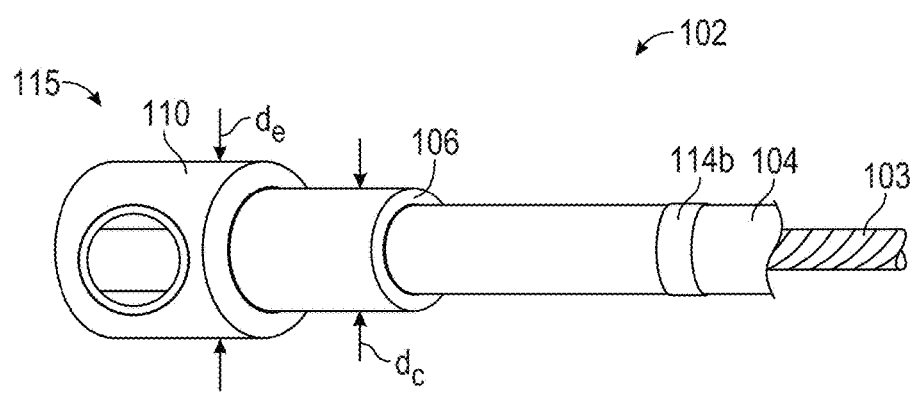

FIG. 3C shows a magnified view of a portion 115 of the emitter assembly 102. The emitter assembly 102 includes an electrode carrier 106 and electrodes 110. The electrode carrier 106 is a moveable overtube, coaxial with the guide wire lumen 104 and the guide wire 103, aligned with the central axis 107. In some embodiments, the electrode carrier 106 is flexible, having an inner diameter $d_c$ of about 0.025 inches. In the example shown, bipolar electrodes 110 are in the form of pairs of co-axial cylinders separated by an internal insulating layer. The electrodes 110 are wrapped around, or otherwise mounted to, the electrode carrier 106. The exemplary cylindrical electrodes 110 have outer diameters $d_e$ of about 0.030 inches. In some embodiments, unipolar electrodes, low profile electrodes, or emitter electrodes of any other suitable design may be used. The electrodes 110 are powered via the electrical wires 132 that extend along the electrode carrier 106, e.g., in a groove formed on an outside surface of the electrode carrier 106, as is known in the art (see, for example, U.S. Pat. No. 8,888,788, which shows similar wiring grooves on an outside surface of a catheter). The electrical wires 132 are coupled by the connector 129 to an external generator, e.g., an external high voltage pulse generator. There may be slack in the electrical wires at the connector 129 to allow advancement of the electrode carrier 106. Two markers, e.g., marker bands 114a,b, are provided on a surface of the guide wire lumen 104, marking destination locations inside the angioplasty balloon 105. In some embodiments, the marker bands 114a,b are crimped onto the guide wire lumen 104. In some embodiments, the marker bands 114a,b are glued onto the guide wire lumen 104.

Figure 3D:
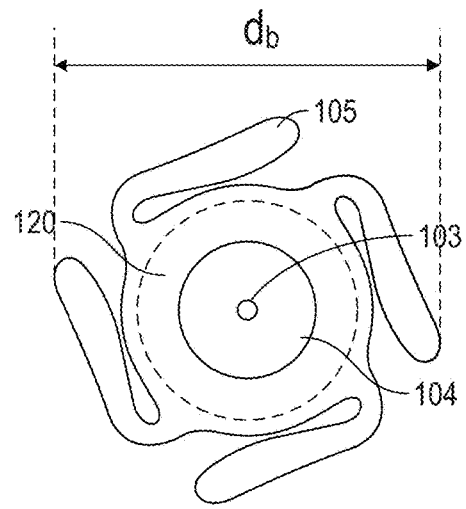

FIG. 3D illustrates an end view from the distal end of the translatable shock wave treatment apparatus 100, showing the guide wire 103, the guide wire lumen 104, and the folded angioplasty balloon 105. The angioplasty balloon 105 may be wrapped in a clockwise or counterclockwise arrangement to facilitate unobstructed inflation, as is known in the art. In some embodiments, the guide wire lumen 104 has an outer diameter equal to about 0.023 inches and the guide wire 103, the guide wire lumen 104, and the folded angioplasty balloon 105, together have an outer diameter $d_b$ that is as small as 0.032 inches, i.e., less than 1.0 mm.

Figure 4:
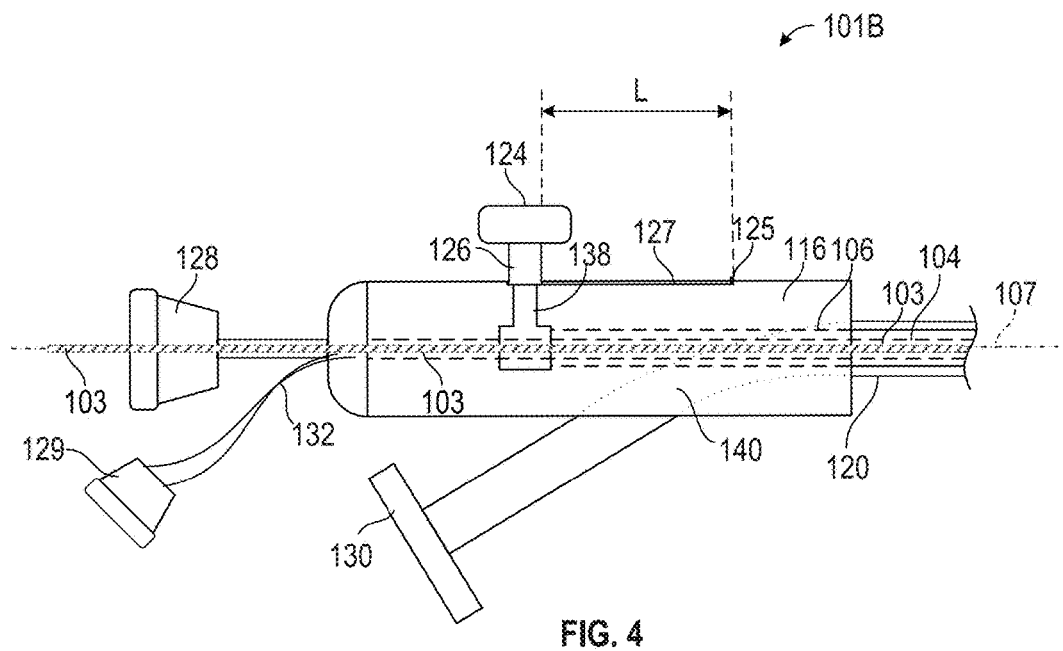
FIG. 4 is a magnified side elevation view of a handle assembly of the translatable shock wave treatment apparatus shown in FIG. 2B.

FIG. 4 shows a magnified view of an exemplary handle assembly 101B, according to some embodiments of the present disclosure. The handle assembly 101B, like the handle assembly 101A, is operable to move the emitter assembly 102 relative to the angioplasty balloon 105. In the over-the-wire embodiment of the translatable shock wave treatment apparatus 90, the handle assembly 101B is further operable to move the guide wire 103 relative to a receiving vascular structure. The handle assemblies 101A,B include a housing 116, an inflation lumen 120, an electrode carrier handle 124, a stop 125, a post 126, a slot 127 of length L, and the connector 129. The handle assembly 101B further includes the guide wire handle 128. The housing 116 is generally cylindrical, but may have a cross-section of arbitrary shape e.g., a round cylinder, a square cylinder, a triangular cylinder, or the like. The inflation lumen 120 is operable to inflate the angioplasty balloon 105, via a channel, with a fluid, e.g., a conducting fluid 140. The conducting fluid 140 may be, for example, saline solution or another electrolytic solution. Inflation of the angioplasty balloon 105 occurs when an inflation port 130 pressurizes the conducting fluid, causing the conducting fluid to flow through the inflation lumen 120. The inflation lumen 120 may be, for example, a tube or channel that extends through the housing 116 and along the central axis 107, into the angioplasty balloon 105. The inflation lumen 120 has a volume that is in fluid communication with an interior volume of the angioplasty balloon 105, as shown in FIGS. 3A and 3D. The inflation lumen 120 may be coaxial with the guide wire lumen 104 and the guide wire 103 as shown in FIG. 4, or the inflation lumen 120 may be within the guide wire lumen 104, alongside the guide wire 103, as is known in the art.

In some embodiments, the guide wire handle 128 is attached to the proximal end of the guide wire 103. The guide wire 103 is inserted into a vascular structure by manually pushing the guide wire handle 128 toward the housing 116, as is known in the art. The connector 129 is attached to wires 132. The connector 129 couples the external generator that supplies electrical power, e.g., in the form of high voltage pulses, to the emitter assembly 102 via the wires 132. The electrode carrier handle 124 is used to align the emitter assembly 102 with respect to the angioplasty balloon 105. The emitter assembly 102 is initially positioned outside the angioplasty balloon 105. As the electrode carrier handle 124 is manually advanced through the slot 127 toward the stop 125, the emitter assembly 102 translates along the guide wire lumen 104 to a position inside the angioplasty balloon 105, as will be described in greater detail below. In some embodiments, when the electrode carrier handle 124 is moved all the way to the stop 125 through the distance L, the electrode carrier 106 extends between the marker bands 114a,b, which are also separated by a distance approximately equal to L. The distance L may be about 15 mm.

A position of the electrode carrier handle 124 opposite the stop 125 corresponds to a position of the emitter assembly 102 that is outside the inflated angioplasty balloon 105. The electrode carrier handle 124 is coupled to the electrode carrier 106 by a pusher 138, made of a semi-rigid material. In some embodiments, the pusher 138 is a nitinol rod having a diameter of about 0.010 inches. The pusher 138 is internal to the housing 116. As the post 126 slides through the slot 127 toward the stop 125, the pusher 138 causes the emitter assembly 102 to translate forward along the central axis 107, relative to the angioplasty balloon 105.

FIG. 5 shows the translatable shock wave treatment apparatus 100 after advancing the guide wire lumen 104 and at least partially inflating the angioplasty balloon 105, according to some embodiments of the present disclosure. As the angioplasty balloon 105 inflates, it unfolds to form a volume surrounding the guide wire lumen 104. The inflated angioplasty balloon 105 may be elongated as shown, or it may have a more spherical shape. In FIG. 5, the emitter assembly 102 is shown in an initial position outside the inflated angioplasty balloon 105. The angioplasty balloon 105 may be inflated just enough to allow the emitter assembly 102 to be inserted into the balloon. In some embodiments, the emitter assembly 102 includes one or more wires 132 e.g., copper leads, of a flexible circuit that wraps around the electrode carrier 106, e.g., in a spiral configuration. Emitters may be stationed at locations along the wires 132 instead of being in the form of cylindrical electrodes 110.

FIG. 6 shows a magnified cut view of the distal end of the guide wire lumen 104, according to some embodiments of the present disclosure. The emitter assembly 102 may reside within or adjacent to the inflation lumen 120, and is positioned outside the inflated angioplasty balloon 105. The emitter assembly 102 has a distal end 134 that will align with a first marker band 114a after the electrode carrier 106 is moved inside the angioplasty balloon 105. The emitter assembly 102 also has a proximal end 136 that will align with a second marker band 114b when the electrode carrier 106 is moved inside the angioplasty balloon 105.

Figure 7:
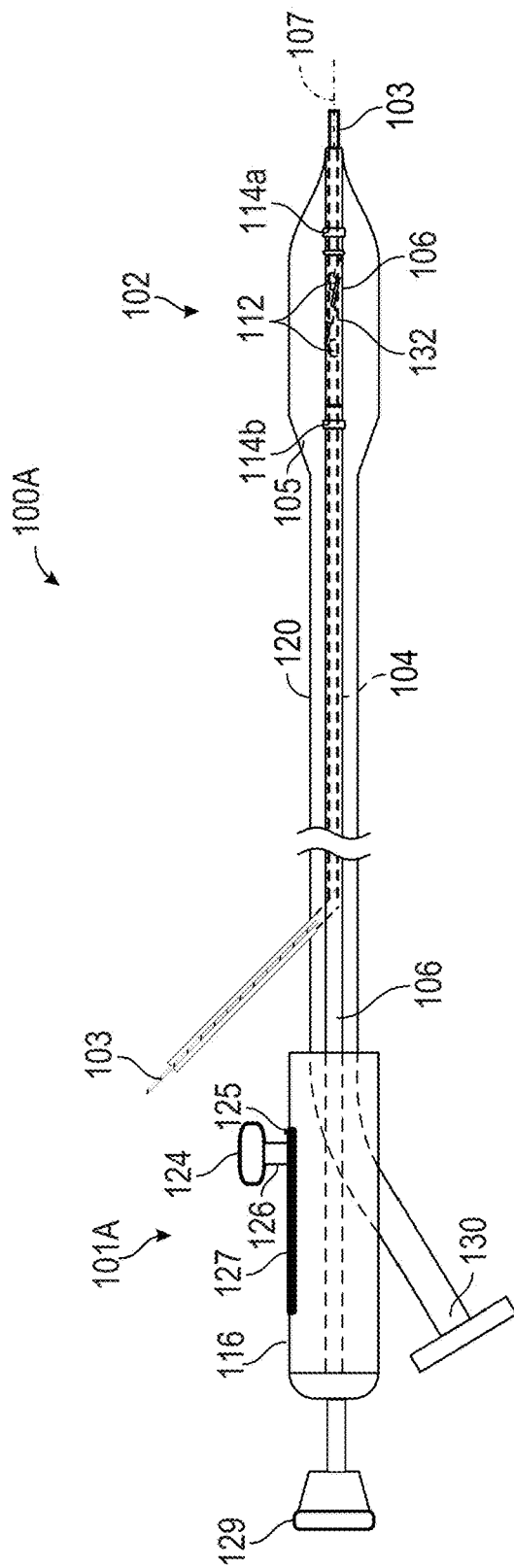
FIG. 7 is a side elevation view of the translatable shock wave treatment apparatus of FIGS. 3A-3D in a final position.

FIG. 7 shows the translatable shock wave treatment apparatus 100, in which the electrode carrier 106 has been moved inside the angioplasty balloon 105, so that the ends of the electrode carrier 106 coincide with the marker bands 114a,b. Accordingly, the electrode carrier handle 124 has been moved along the slot 127 to a position that coincides with the stop 125. The electrodes 110 may be of the design shown in FIG. 6 or of the design shown in FIG. 3B.

Figure 8:
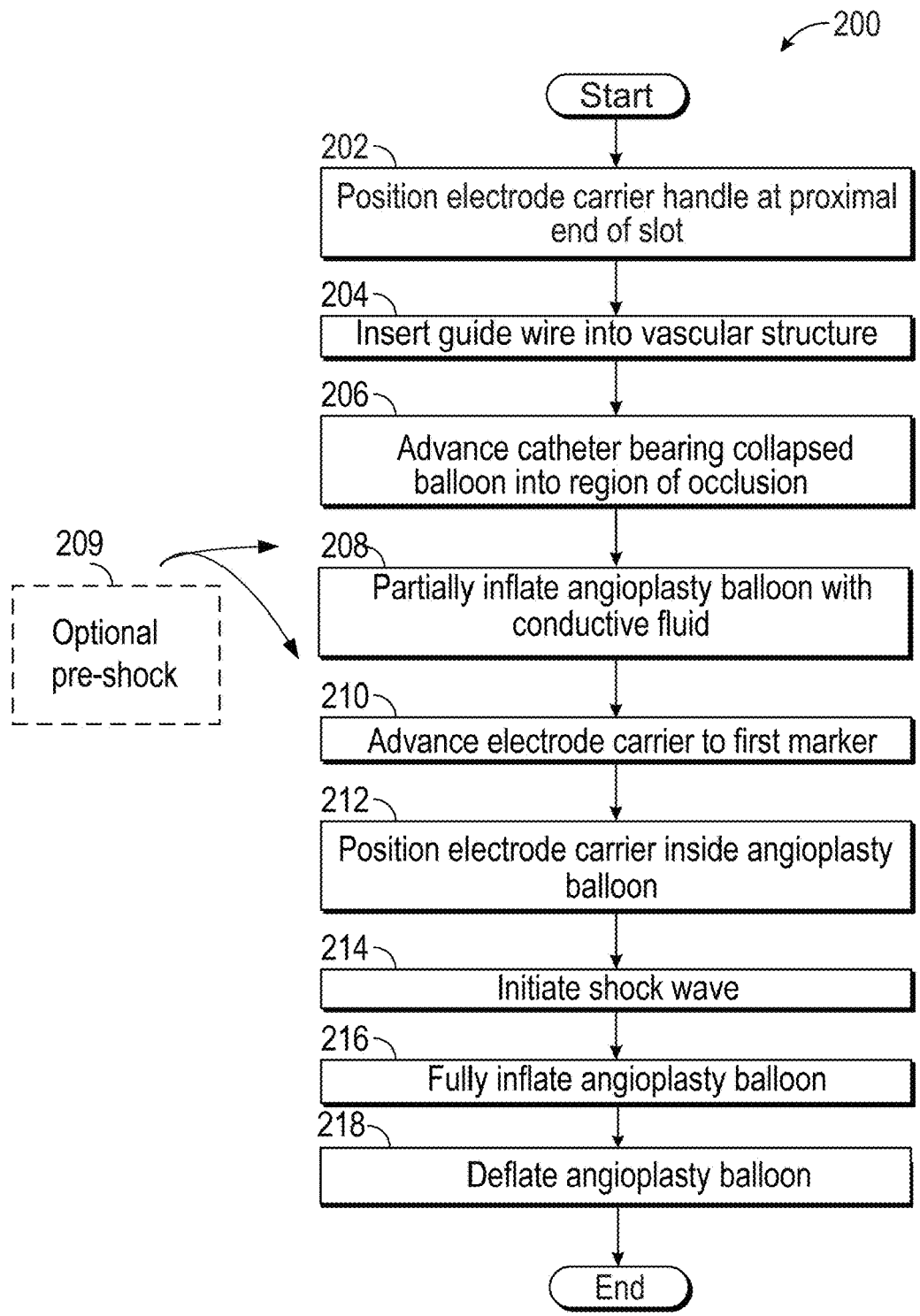
FIG. 8 is a flow diagram of a method of treating calcified lesions using the translatable shock wave treatment apparatus shown in FIGS. 3-7, according to some embodiments of the present disclosure as described herein.

FIG. 8 shows a sequence of steps illustrating a shock wave therapy technique, according to some embodiments of the present disclosure. The shock wave therapy technique entails executing a method 200 using the translatable shock wave treatment apparatus 100, as described below and illustrated in FIGS. 9-13.

At step 202, the translatable shock wave treatment apparatus 100 is prepared for insertion into the blood vessel 50. The guide wire handle 128 is pulled behind the housing 116 to a retracted position, and the electrode carrier handle 124 slides to its initial position at the proximal end of the slot 127, opposite the stop 125.

At step 204, the guide wire 103 is inserted into the target vascular structure, e.g., the blood vessel 50, as shown in FIG. 9.

At step 206, the guide wire 103 is advanced ahead of the guide wire lumen 104, through the blood vessel 50 using the guide wire handle 128. The tip of the guide wire lumen 104 bearing the folded angioplasty balloon 105 is positioned in an occluded region of the blood vessel 50 that has lesions 54 and, in particular, calcifications 56, as shown in FIG. 9. The guide wire lumen 104 is then advanced until the marker bands 114a,b are aligned with the occluded region to be treated. In the occluded region, the smallest diameter, $D_1$ of the blood vessel 50 may accommodate the guide wire lumen 104 and the folded balloon 105, while being too small to accommodate insertion of the electrode carrier 106. Accordingly, the electrode carrier handle 124 remains at an initial position opposite the stop 125 so that the electrode carrier 106 temporarily remains outside the angioplasty balloon 105.

At step 208, the angioplasty balloon 105 is inflated, at least partially, expanding outward from its folded position around the guide wire lumen 104, as shown in FIG. 10. Inflation occurs as the angioplasty balloon 105 is filled with the conducting fluid 140 by pumping the conducting fluid 140 through the inflation lumen 120 using the inflation port 130. The inflated angioplasty balloon 105 pre-dilates the occluded region of the blood vessel 50 by compressing soft portions of the lesion 54, while the calcifications 56 resist inflation of the angioplasty balloon 105. Inflation of the angioplasty balloon 105 opens the interior diameter of the blood vessel 50 to a diameter $D_2$ that exceeds the diameter $d_c$ of the electrode carrier 106 bearing the electrodes 110.

At step 210, the guide wire lumen 104 is advanced further into the pre-dilated blood vessel 50 so as to align the distal end 134 of the emitter assembly 102 with the second marker band 114b. Optionally, the angioplasty balloon 105 may be further inflated one or more times after advancing the guide wire lumen 104. Steps 208-210 may be repeated to ensure that the diameter $D_2$ will accommodate the electrode carrier 106 and the electrodes 110.

Figure 11:
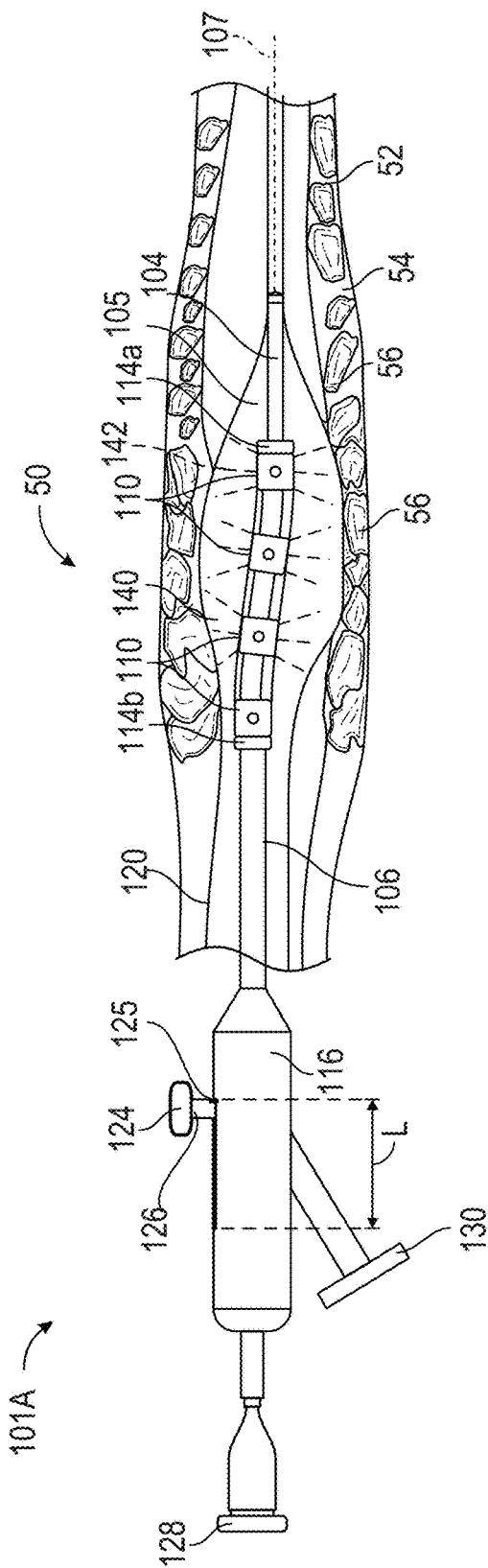

At step 212, once the diameter $D_2$ is enlarged, the electrode carrier handle 124 is advanced by sliding the post 126 along the slot 127 through the full distance L, to the stop 125. The distal end 134 of the emitter assembly 102 is then aligned with the first marker band 114a and the proximal end 136 of the emitter assembly 102 is aligned with the second marker band 114b, as shown in FIG. 11. The electrode carrier 106 thus is positioned inside the angioplasty balloon 105 between the first and second marker bands 114a, 114b, which are stationed at destination locations along the guide wire lumen 104. Optionally, the electrode carrier 106 may be rotated to align one or more of the emitters closer to the calcifications 56 in a target area of the vessel wall 52. Once the electrode carrier 106 is in position, the angioplasty balloon 105 may be deflated for about 30 seconds to allow blood to flow, followed by re-inflating the angioplasty balloon 105 to a pressure of about four atmospheres.

Figure 12:
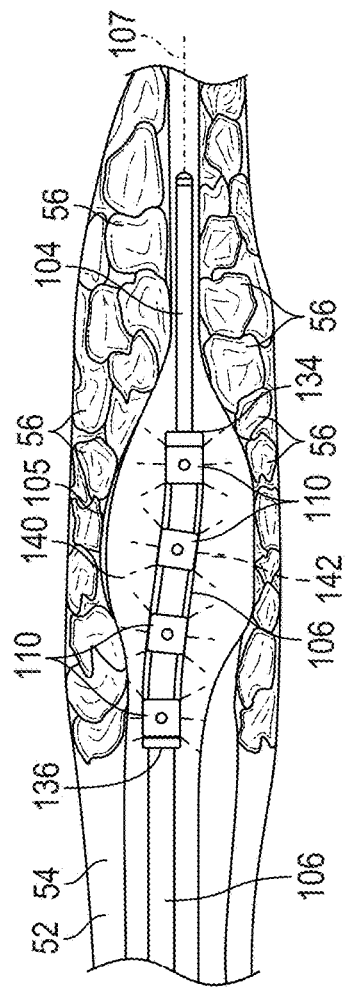

At step 214, a shock wave is initiated by applying an electrical signal, e.g., a high voltage pulsed signal, to the electrodes 110. The high voltage pulsed signal causes the emitters to arc, either to one another or to the conducting fluid 140, depending on a relative polarity and spacing between the emitters. In some embodiments, the electrodes 110 are unipolar and the conducting fluid acts as a second pole. In some embodiments, pairs of emitters, or bipolar electrodes, are positioned close to one another, e.g., spaced apart about 4-15 millimeters along the wires 132. A pulsing gap between negative and positive poles within each pair may be in the range of about 0.0005-0.02 inches so that an arc occurs across the pulsing gap. Heat from the arcing event vaporizes and then ionizes a small volume of the conducting fluid 140, creating a rapidly expanding region of plasma around the energized electrodes 110. Such rapid expansion initiates a shock wave 142 that propagates out from each electrode 110 through the conducting fluid 140, as shown in FIGS. 11 and 12. As the shock waves 142 in the conducting fluid 140 impinge upon the vessel walls 52, shock wave energy is transmitted to the lesions 54. The shock wave energy breaks apart the calcifications 56, thereby softening the lesions 54. In some embodiments of the method 200, the high voltage pulsed signal may include, for example, between five and twenty pulses.

Figure 13:
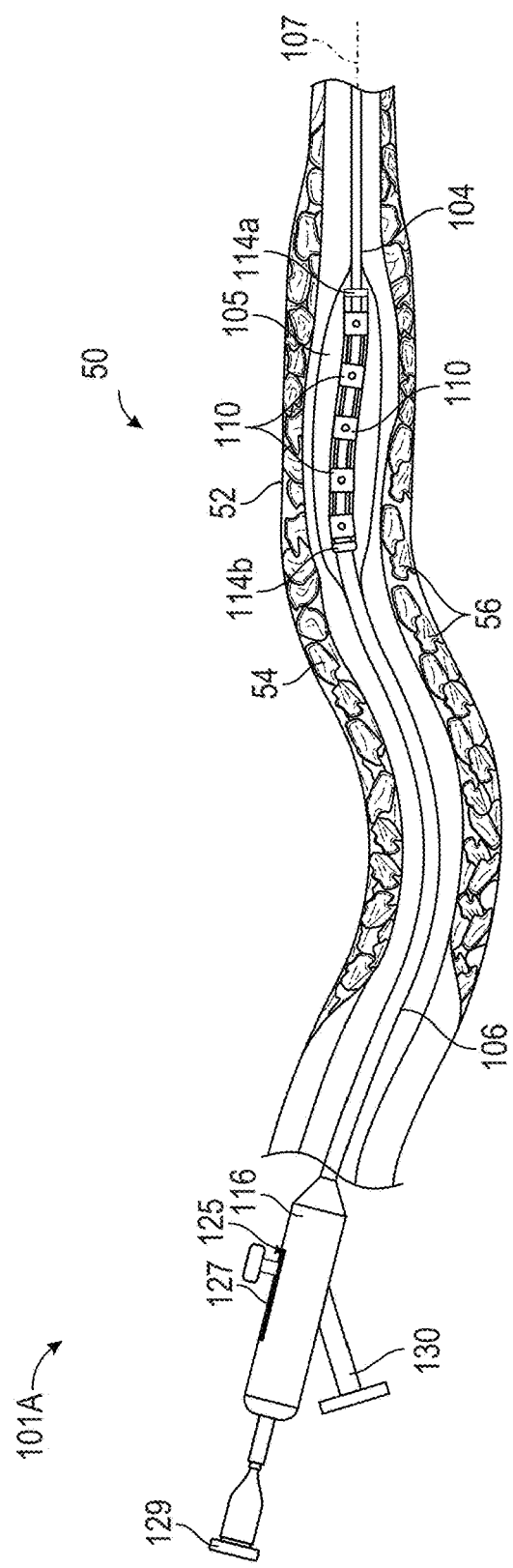

At step 216, the angioplasty balloon 105 is fully inflated to compress the softened lesions 54 against the vessel wall 52, thus restoring blood flow within the blood vessel 50, as shown in FIG. 13. The angioplasty balloon 105 may be deflated for about 30 seconds, and then re-inflated to a pressure of about six atmospheres for about 30 seconds.

Steps 214 and 216 may be repeated one or more times until the calcifications 56 are broken into small pieces and blood flow within the blood vessel 50 is restored to about 90%. In some embodiments of the method 200, 8-10 such cycles are performed so as not to interrupt blood flow for an extended period of time. When treating coronary arteries, performing the angioplasty procedure in short cycles may prevent syncope. When treating peripheral arteries performing the angioplasty procedure in short cycles may prevent swelling.

At step 218, following treatment, the angioplasty balloon 105 is deflated by de-pressurizing the conducting fluid 140 using the inflation port 130. The guide wire lumen 104 is removed from the blood vessel 50 and the guide wire handle 128 is then pulled away from the housing 116 to retract the guide wire 103.

In some instances, the blood vessel 50 is so occluded that shock waves 142 are needed to create an opening that permits full inflation of the angioplasty balloon 105 and, subsequently, full insertion of the electrode carrier 106 into the angioplasty balloon 105. In such cases, an additional step 209 may be inserted before or after step 208 in the method 200. At step 209, an optional pre-shock treatment may be applied from a position slightly outside the balloon 105, or outside the severely obstructed region, as shown in FIG. 12. The pre-shock treatment is carried out in a similar fashion as the shock treatment described above in step 214. The optional pre-shock treatment dilates the blood vessel 50 so that the electrode carrier 106 can be slidably advanced further into the occluded region in an incremental fashion, to allow repeated application of the shock waves 142. By alternating shock wave therapy with inflation of the angioplasty balloon 105, it is possible to treat an extended calcified lesion 54 along the length of the blood vessel 50.

The foregoing description, for purpose of explanation, has been made with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The invention claimed is:

1. An apparatus, comprising:
   an elongate member having a distal end and a proximal end and including a central lumen for receiving a guide wire;
   a balloon attached to the distal end of the elongate member;
   a cylindrical member carrying a plurality of electrodes said member being, slidable along and over a length of the elongate member from an initial position outside the balloon to a destination position wherein the electrodes are positioned inside the balloon.

2. The apparatus of claim 1, further comprising an inflation device operable to inflate the balloon to a diameter exceeding that of the elongate member.

3. The apparatus of claim 1, further comprising a channel configured to direct fluid into the balloon.

4. The apparatus of claim 1, further comprising a handle coupled to the electrode carrier, the handle being operable to slide the electrode carrier along the length of the elongate member.

5. The apparatus of claim 4 wherein the handle is disposed at the proximal end of the elongate member.

6. The apparatus of claim 1 wherein the elongate member is suitable for introduction into a blood vessel.

7. The apparatus of claim 6 wherein a diameter of the elongate member is less than 2.0 mm.

8. The apparatus of claim 1 wherein the electrode carrier further comprises emitters stationed at surface locations of the electrode carrier.

9. The apparatus of claim 8, further comprising a high voltage pulse generator electrically coupled to the emitters.

10. The apparatus of claim 9 wherein each emitter, when energized by the high voltage pulse generator, transmits a current by arcing.

11. The apparatus of claim 1, further comprising one or more markers stationed at destination locations along the distal end of the elongate member.

12. A method, comprising:
   providing a balloon attached to a distal end of an elongate member;
   providing an electrode carrier slidably mounted on the elongate member at a position outside of, and proximal to, the balloon, the electrode carrier including an emitter attached thereto;
   advancing the balloon into a portion of a vascular structure to be treated;
   partially inflating the balloon with a fluid;
   translating the electrode carrier along the elongate member to a position at least partially inside the balloon; and
   initiating a shock wave in the fluid by energizing the emitter.

13. The method of claim 12 wherein translating the electrode carrier entails, prior to the initiating step, sliding the electrode carrier along a length of the elongate member so that the electrode carrier is fully inside the balloon.

14. The method of claim 12 wherein the elongate member is a catheter.

15. The method of claim 12 wherein translating the electrode carrier further includes aligning the electrode carrier with a marker.

16. The method of claim 12 wherein inflating the balloon increases an inside diameter of the vascular structure.

17. The method of claim 12, further comprising, prior to inflating the balloon, rotating the electrode carrier so as to position the emitter adjacent to a target area of the vascular structure.

18. The method of claim 12 wherein the vascular structure includes one or more of a coronary artery, a peripheral artery, and a valve.

19. The method of claim 12, further comprising further inflating the balloon after initiating the shock wave.

20. The method of claim 19, further comprising when the electrode carrier is only partially inside the balloon, translating the electrode carrier further inside the balloon and repeating initiating the shock wave.

21. A device for use in an angioplasty procedure, the device comprising:
   an elongate member having a distal end and a proximal end, the elongate member extending linearly along a central axis;

a balloon attached to the distal end of the elongate member;

an inflation pump attached to the proximal end of the elongate member, the inflation pump in fluid communication with the balloon;

an electrode carrier translatable along the elongate member from the proximal end of the elongate member outside the balloon to a position within the balloon;

a plurality of electrodes attached to the electrode carrier; and a high voltage pulse generator electrically coupled to the electrodes, the high voltage pulse generator causing the electrodes to arc and propagate a shock wave within the balloon.

22. The device of claim 21, further comprising a marker at a destination position on the elongate member.

23. The device of claim 21, further comprising a handle coupled to the electrode carrier.

\* \* \* \* \*